(12) United States Patent
Curry

(10) Patent No.: US 8,765,642 B2
(45) Date of Patent: Jul. 1, 2014

(54) COMBINATORIAL PROBE LIBRARIES

(75) Inventor: Bo U. Curry, Redwood City, CA (US)

(73) Assignee: Agilent Technolgies, Inc., Santa Clara, CA (US)

( * ) Notice: Subject to any disclaimer, the term of this patent is extended or adjusted under 35 U.S.C. 154(b) by 0 days.

(21) Appl. No.: 13/448,985

(22) Filed: Apr. 17, 2012

(65) Prior Publication Data

US 2013/0274118 A1    Oct. 17, 2013

(51) Int. Cl.
*C40B 40/00* (2006.01)

(52) U.S. Cl.
USPC .......................................................... 506/13

(58) Field of Classification Search
None
See application file for complete search history.

(56) References Cited

U.S. PATENT DOCUMENTS

| | | |
|---|---|---|
| 5,985,549 A | 11/1999 | Singer et al. |
| 6,506,563 B1 | 1/2003 | Ward et al. |
| 6,551,780 B1 | 4/2003 | Bastian et al. |
| 6,821,770 B1 * | 11/2004 | Hogan ........................ 435/287.2 |
| 2007/0059747 A1 | 3/2007 | Bastian et al. |
| 2007/0238105 A1 | 10/2007 | Barrett et al. |
| 2010/0081131 A1 | 4/2010 | Ach et al. |
| 2010/0221708 A1 | 9/2010 | Yamada et al. |

\* cited by examiner

*Primary Examiner* — Tracy Vivlemore
*Assistant Examiner* — Karen S Weiler

(57) ABSTRACT

Provided herein is a set of reagents comprising: a plurality of at least three probe libraries, wherein each library of the plurality comprises one or more probe sets that are each specific for a target; and at least one of the libraries comprises a probe set that is present in another of the libraries. The plurality of libraries can be hybridized to spatially separated targets, simultaneously or sequentially. The identity of a spatially separated target can be determined by identifying which combination of the multiple libraries hybridize thereto.

11 Claims, 1 Drawing Sheet

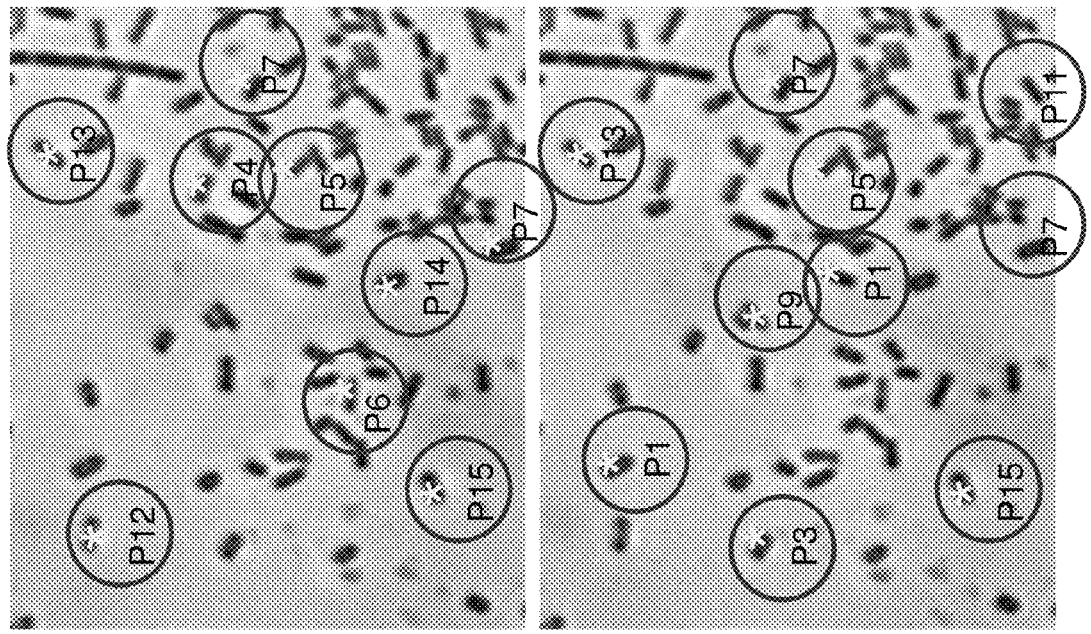
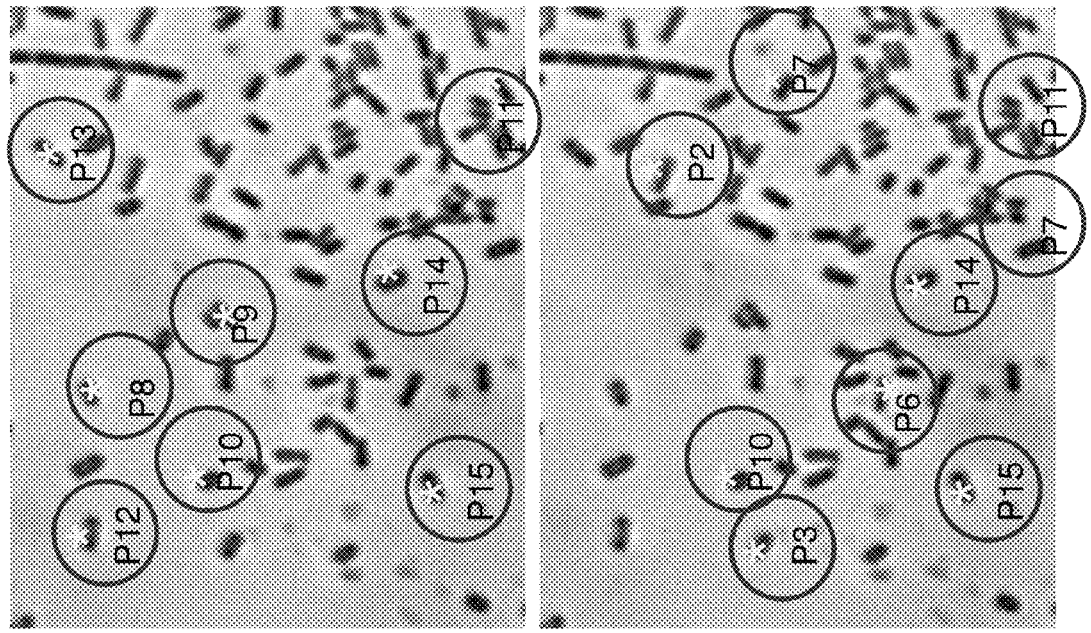

COMBINATORIAL PROBE LIBRARIES

INTRODUCTION

Many detection assays involve contacting a labeled target-specific probe (e.g., a labeled nucleic acid or labeled antibody) with a sample under conditions suitable for binding of the probe to its target in the sample. After unbound probe is removed, e.g., by washing, the signal emanating from probe's label is detected. Detection of the label indicates that the target is in the sample. The position of the label's signal can indicate the position of a target in a sample. In one example, probes can be used to analyze fixed cells in order to identify which microbes are present in a sample. The rapid identification of microbes is of great importance in clinical diagnosis, public health, veterinary health, biodefense, environmental science, and agriculture.

BRIEF DESCRIPTION OF THE FIGURES

FIG. 1 shows prophetic results that could be obtained using the combinatorial probe library shown in Table 1 below.

DEFINITIONS

The term "sample" as used herein relates to composition that contains a plurality of targets, where the term "target" refers to a biological entity that can be spatially separated, hybridized to a probe, and visualized. Cells, individual chromosomes, and material deposited in an array are examples of targets.

The term "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the like.

The term "nucleic acid" refers to a polymer of any length, e.g., greater than about 2 bases, greater than about 10 bases, greater than about 100 bases, greater than about 500 bases, greater than 1000 bases, up to about 10,000 or more (e.g., 100,000,000 or more) bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "oligonucleotide" as used herein denotes a single stranded multimer of nucleotide of from about 2 to about 500 nucleotides. Oligonucleotides may be synthetic or may be made enzymatically. Oligonucleotides may contain ribonucleotide monomers (i.e., may be oligoribonucleotides), deoxyribonucleotide monomers or a combination of the two. Oligonucleotides may be 10 to 20, 11 to 30, 31 to 40, 41 to 50, 51-60, 61 to 70, 71 to 80, 80 to 100, 100 to 150, 150 to 200 or 200-250 or up to 500 nucleotides in length.

An "array", includes any two-dimensional or substantially two-dimensional (as well as a three-dimensional) arrangement of addressable regions, e.g., spatially addressable regions or optically addressable regions, bearing nucleic acids, particularly oligonucleotides or synthetic mimetics thereof, and the like. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a surface of the substrate. Depending upon the use, any or all of the arrays may be the same or different from one another and each may contain multiple spots or features. An array may contain one or more, including more than two, more than ten, more than one hundred, more than one thousand, more ten thousand features, more than one hundred thousand features, up to one million features, or more, in an area of less than 20 cm$^2$ or even less than 10 cm$^2$, e.g., less than about 5 cm$^2$, including less than about 1 cm$^2$, less than about 1 mm$^2$, e.g., 100 µm$^2$, or even smaller. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 mm and less than 1.5 mm, such as more than about 0.8 mm and less than about 1.2 mm.

Arrays can be fabricated using drop deposition from pulse-jets of either precursor units (such as nucleotide monomers) in the case of in situ fabrication, or a previously made nucleic acid. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

An array is "addressable" when it has multiple regions of different moieties (e.g., different oligonucleotide sequences) such that a region (i.e., a "feature" or "spot" of the array) at a particular predetermined location (i.e., an "address") on the array contains a particular sequence. Array features are typically, but need not be, separated by intervening spaces.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent. "Determining the identity" includes assigning something a descriptor that identifies it, e.g., determining the identity of a microbe refers to assigning it a descriptor that indicates its common name, scientific name, code, family, genus, species, strain, or genotype.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end.

The term "microbe", as used herein, refers to a microorganism. The term includes bacteria, fungi, archaea, and protists. The term "microbe" includes pathogenic bacteria, causing diseases such as plague, tuberculosis and anthrax; protozoa, causing diseases such as malaria, sleeping sickness and toxoplasmosis; and also fungi causing diseases such as ringworm, candidiasis or histoplasmosis, for example.

The term "in situ" refers to "inside a cell". For example, the RNA being detected by in situ hybridization is present inside a cell. The cell may be permeabilized or fixed, for example.

The term "hybridization" refers to the specific binding of a nucleic acid to a complementary nucleic acid via Watson-Crick base pairing. Accordingly, the term "in situ hybridization" refers to specific binding of a nucleic acid to a complementary nucleic acid inside a cell or in an intact chromosome. The terms "hybridizing" and "binding", with respect to nucleic acids, are used interchangeably.

The term "contacting" means to bring or put together. As such, a first item is contacted with a second item when the two items are brought or put together, e.g., by touching them to each other or combining them in the same solution.

The term "in situ hybridization conditions" as used herein refers to conditions that allow hybridization of a nucleic acid to a complementary nucleic acid, e.g., a sequence of nucleotides in a RNA or DNA molecule and a complementary oligonucleotide, in a cell. Suitable in situ hybridization conditions may include both hybridization conditions and optional wash conditions, which conditions include temperature, concentration of denaturing reagents, salts, incubation time, etc. Such conditions are known in the art.

The terms "ribonucleic acid" and "RNA" as used herein refers to a polymer composed of ribonucleotides.

The phrase "different RNA molecules" as used herein refers to RNA molecules that have different nucleotide sequences, e.g., different RNA molecules are transcribed from different genes.

The term "sites", as used in the context of a site in a nucleic acid molecule, refers to a contiguous sequence of nucleotides in the nucleic acid molecule.

The phrase "labeled polynucleotide" refers to a polynucleotide that contains a detectable moiety. The detectable moiety may produce a signal directly or indirectly. One example of a detectable moiety that produces a signal directly is a fluorescent molecule. Detectable moieties that produce a signal indirectly include moieties that produce a signal upon exposure to detection reagents such as substrates or antibodies, etc. A detectable moiety that produces a signal directly can optionally be detected by indirect means such as by using a labeled antibody that binds to the moiety. In certain cases, a signal may be of a particular wavelength that is detectable by a photodetector, e.g., a light microscope, a spectrophotometer, a fluorescent microscope, a fluorescent sample reader, or a florescence activated cell sorter, etc.

The term "unique" refers to a characteristic that is only found in members of one type of a class, species, etc. For example, "a binding site unique to a microbe" or a grammatical equivalent thereof, refers to a contiguous sequence of nucleotides that is found only in microbes that belong to the same genus, same species, or same strain. Thus, a unique sequence allows the identification of a microbe as a particular genus, species, or strain.

The term "predetermined" refers to something that is known before use.

The phrase "different microbes" is used interchangeably with "different types of microbes". These phrases refer to microbes that are distinct from each other because they belong to a different genus, or to a different species or to a different strain. Two microbes that belong to different genus are considered to be different, microbes that belong to the same genus but to different strains are considered to be different, microbes that belong to the same genus and species but to different strains are also considered to be different.

The phrase "associated with" refers to the situation where a characteristic of a first thing is imparted to a second thing such that the second thing then has that characteristic. For example, a signal associated with a microbe refers to a signal that comes from the microbe by virtue of labeled polynucleotides being hybridized to the RNA of the microbe. Similarly, an optically detectable signature associated with a microbe refers to the signature which the microbe has by virtue of labeled polynucleotides being hybridized to the RNA of the microbe.

The term "matching" refers to the process of comparing one thing to another to find a match. For example, once the instant method has been performed and which libraries hybridize to a target have been determined, the identity of the target may be determined matching a "code" which indicates which libraries hybridized to the target (e.g., 1010), with a code in a look-up table.

The terms "plurality", "set", "population" and "multiple" are used interchangeably to mean at least 2, at least 10, at least 100, at least 500, at least 1000, at least 10,000, at least 100,000, up to at least 1,000,000, or 10,000,000 or more.

The phrase "distinguishable labels" or any grammatical equivalent thereof refers to labels can be independently detected and measured, even when the labels are mixed. In other words, the amounts of label present (e.g., the amount of fluorescence) for each of the labels are separately determinable, even when the labels are co-located (e.g., in the same tube or in the same duplex molecule or in the same cell). Suitable distinguishable fluorescent label pairs include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 and TOPRO3 (Molecular Probes, Eugene, Oreg.). Further suitable distinguishable detectable labels may be found in Kricka et al. (Ann Clin Biochem. 39:114-29, 2002).

The term "target-specific probe set" refers to a set of probes that specifically hybridize to unique sequences in a target and allow the identity of a target to be identified. In the context of microbe identification, a target specific probe set allows a microbe to be identified as being of a particular genus, species, or strain to be determined. The individual polynucleotides within each target-specific probe set do not need to hybridize to the same target molecule (e.g., the same cDNA or chromosome) in a sample.

The term "target-specific polynucleotide", refers to a polynucleotide probe, e.g., an oligonucleotide or other sequence, e.g., a BAC, cDNA or any other probe such as a PCR product, that specifically hybridizes to a unique sequence in a target and allows the identity of the target to be identified.

A single "target-specific probe set", as defined above, contains one or more polynucleotide probes that all specifically hybridize to the same target (e.g., the same cell).

The individual target-specific probe sets of a "plurality of target-specific probe sets" each hybridize to different targets in a way that distinguishes the targets from one another.

The term "target" refers to a biological entity that can be spatially separated, hybridized to a probe, and visualized. Cells, individual chromosomes, and material deposited in an array are examples of targets.

DESCRIPTION OF EXEMPLARY EMBODIMENTS

Before the present invention is described, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Provided herein is a way of making multiple libraries of probes. The different libraries, when hybridized with a sample containing a plurality of spatially separated targets, allow identities of the targets (e.g., the species or strains of cells, or RNA molecules, or chromosomes) to be determined. The identity of an individual target may be determined by determining which of the libraries hybridize to the target. A set of reagents made by the method is also provided, where the set of reagents comprises: a plurality of at least three probe libraries, (e.g., 4, 5, 6, 7, 8, 9, 10, 11 or 12 libraries), wherein each library of the plurality comprises one or more probe sets that are each specific for a target; and at least one of the libraries comprises a probe set that is present in another of the libraries. In certain cases, each probe set is uniquely defined by the set of libraries that contain the probe set. The plurality of labeled libraries can be hybridized to spatially separated targets, simultaneously or sequentially. The identity of an individual target can be determined by identifying which combination of the multiple libraries hybridize to that target.

In one embodiment, the method comprises combining selected probe sets from a plurality of target-specific probe sets that each comprises a different population of target-specific probes to produce multiple libraries, wherein each library is composed of a different combination of the target-specific probe sets. With reference to Table 1 shown below, the target-specific probe sets in the left hand column "P1", "P2", "P3" etc. are combined in specific, pre-determined ways to produce multiple libraries "L1", "L2", "L3", and "L4", wherein each column below the library number indicates which probe sets were combined to make the library. In this method, probe sets are combined into libraries such that each library comprises some but not all of the probe sets, combined together such that each probe set occurs in a unique combination of libraries. The exemplary embodiment illustrated below shows the production of four libraries from 15 probe sets, using a simple binary code. Pi designates the probe set specific to target i, Lk designates the kth library. Each library contains a specific, pre-determined combination of probe sets. For example, probe set P1 is only present in library L4, whereas probe set P5 is present in libraries L2 and L4 and probe set 15 is present in libraries L1, L2, L3 and L4.

TABLE 1

|    | L1 | L2 | L3 | L4 |
|----|----|----|----|----|
| P1 | 0  | 0  | 0  | 1  |
| P2 | 0  | 0  | 1  | 0  |
| P3 | 0  | 0  | 1  | 1  |
| P4 | 0  | 1  | 0  | 0  |
| P5 | 0  | 1  | 0  | 1  |

TABLE 1-continued

|     | L1 | L2 | L3 | L4 |
|-----|----|----|----|----|
| P6  | 0  | 1  | 1  | 0  |
| P7  | 0  | 1  | 1  | 1  |
| P8  | 1  | 0  | 0  | 0  |
| P9  | 1  | 0  | 0  | 1  |
| P10 | 1  | 0  | 1  | 0  |
| P11 | 1  | 0  | 1  | 1  |
| P12 | 1  | 1  | 0  | 0  |
| P13 | 1  | 1  | 0  | 1  |
| P14 | 1  | 1  | 1  | 0  |
| P15 | 1  | 1  | 1  | 1  |

As noted above, in certain cases each probe set may be uniquely defined by the set of libraries that contain the probe set, meaning that each probe set is in a unique combination of libraries, and the combination of libraries in which the probe set is present defines the probe set. For example, with reference to Table 1 above, probe set 1 (P1) is unique because it is only present in library 4 (L4) (i.e., present in L4 but not present in L1, L2 and L3) Likewise, probe set 7 (P7) is unique because it is present in only libraries 2, 3 and 4 (i.e., present in L2, L3 and L4 but not library L1).

The target-specific probe sets used in the method may each comprise at least 1 target-specific polynucleotide probe (e.g., at least 2, at least 5, at least 10, at least 50, at least 100, up to 1,000 or 10,000 or more probes) that each specifically bind to a particular molecule in the target. For example, a probe set may be a collection of polynucleotides complementary to a target RNA or DNA. A set of polynucleotide probes may contain polynucleotide probes that bind to RNA or DNA molecules of a single type of microbe. In certain embodiments, some of the polynucleotides of a set may be designed to overlap with each other (i.e., so that they are "tiled"). In some cases, the amount of overlap may be dependent upon the length of the polynucleotide. For example, for polynucleotides that are about 20 nucleotides long, the overlap may be at least one nucleotide from one polynucleotide to the next. In certain embodiments the overlap may be two or more nucleotides. For polynucleotide that are about 100 nucleotides long, the overlap may be at least 20 nucleotides from one polynucleotide to the next. In other embodiments, the polynucleotides of a set may be designed to be end-to-end tiled. In other embodiments, the polynucleotides may hybridize to different sequences in a target.

Each set of target-specific probes in a plurality of such probe sets is specific for a different target, e.g., a different microbe, relative to the other sets. Thus, polynucleotides of a first set might bind to different RNA or DNA molecules at sites that are unique to a first microbe; whereas the polynucleotides of a second set might bind to different RNA or DNA molecules of a second microbe, and so on. A plurality of sets may be at least 2, at least 10, at least 100, at least 500, up to 1000, or 10,000 or more different sets and each set is specific for a particular target. In certain embodiments, a plurality of sets may be at least 10-50 sets. The probe sets may be combined to make multiple libraries (e.g., at least 3, at least 4, at least 5, at least 6, at least 7, at least 8, at least 9, at least 10, at least 12, at least 15, at least 20, or at least 30, up to 50 or 100 or more different libraries). If oligonucleotides are used in the subject method, they may be designed using genome sequence information as well as expressed gene sequence information available at several public and private databases, for example. For example, genomic sequence information is available via Microbe Genome Sequencing Project, Department of Energy, U.S.A. and from NCBI. Expressed gene sequence information is available at GenBank. Additionally, expressed gene sequences can be derived from gene expression profiling of microbes of interest. Sequences that are diagnostic for a variety of microbes are known. Since the genome sequences of many organisms, including many bacteria, fungi, plants and animals, e.g., mammals such as human, primates, and rodents such as mouse and rat, are known and some are publicly available (e.g., in NCBI's Genbank database), the design of the target-specific oligonucleotides is within the skill of one of skilled in the art. In particular embodiments, oligonucleotides may be designed using methods set forth in US20040101846, U.S. Pat. No. 6,251,588, US20060115822, US20070100563, US20080027655, US20050282174, U.S. patent application Ser. No. 11/729,505, filed March 2007 or U.S. patent application Ser. No. 11/888,059, filed Jul. 30, 2007 and references cited therein, for example. The target-specific probe sets may be, e.g., chromosome specific or cell type specific, for example.

Once made, the libraries are labeled to produce a plurality of labeled libraries. A polynucleotide may be labeled by any of a number of means well known to those of skill in the art. In certain embodiments, a label may be simultaneously incorporated during an amplification step. Thus, for example, polymerase chain reaction (PCR) with labeled primers or labeled nucleotides will provide a labeled amplification product. In certain embodiments, a label may be linked directly to a polynucleotide or to the amplification product after the amplification is completed. Means of attaching labels to nucleic acids are well known to those of skill in the art and include, for example nick translation or end-labeling, by kinasing of the nucleic acid and subsequent attachment of a nucleic acid linker joining the oligonucleotides to a label. In certain cases, a polynucleotide may by labeled using the Universal Linkage System (ULS™, KREATECH Diagnostics; van Gijlswijk et al Universal Linkage System: versatile nucleic acid labeling technique Expert Rev. Mol. Diagn. 2001 1:81-91). In brief, ULS™ labeling is based on the stable binding properties of platinum (II) to nucleic acids. The ULS molecule consists of a monofunctional platinum complex coupled to a detectable molecule of choice. Alternative methods may be used for labeling polynucleotides are set forth in, for example, Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.).

Suitable labels include fluorescent dyes that include xanthene dyes, e.g. fluorescein and rhodamine dyes, such as fluorescein isothiocyanate (FITC), 6-carboxyfluorescein (commonly known by the abbreviations FAM and F),6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R6G$^6$ or G$^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in some applications include: pyrene, coumarin, diethylaminocoumarin, FAM, fluorescein chlorotriazinyl, R110, eosin, JOE, R6G, tetramethylrhodamine, TAMRA, lissamine, ROX, napthofluorescein, Texas red, napthofluorescein, Cy3, and Cy5, etc. Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (Ann Clin Biochem. 39:114-29, 2002).

After labeling, the labeled libraries are hybridized to a sample that contains spatially separated targets. In some embodiments, all of the libraries are labeled with the same label. For example, with reference to the table above, L1, L2, L3 and L4 may be labeled with a first label (e.g., Cy5 or Cy3). In other embodiments, all of the libraries are labeled with the different labels. For example, with reference to the table above, L1 is labeled with a first label, L2, is labeled with a second label L3 is labeled with a third label and L4 is labeled with a fourth label, where the first, second, third and fourth labels are distinguishable from one another.

If the libraries are distinguishably labeled, then they can be hybridized to the spatially-separated targets simultaneously (i.e., at the same time, in the same hybridization reaction). If the libraries are labeled with the same label, they can be hybridized to the spatially-separated targets sequentially (i.e., one after the other, where, after each hybridization, the sample is read, the probes are stripped from the sample, and the sample is re-hybridized with a different library). Spatially separated targets include, e.g., fixed cells, isolated chromosomes and individual RNA molecules within a single cell. Libraries may be hybridized to the sample separately, with a separate measurement made of the positions of signals when hybridized with each library. In one embodiment, the libraries are hybridized successively, measured, then washed away to allow the sample to be hybridized to the next library. In another embodiment, the libraries are labeled with different distinguishable fluorescent dyes, or combinations of fluorescent dyes, and hybridized together. These schemes can also be mixed, by for example hybridizing four libraries each labeled with one of four distinguishable dyes, measuring the spots, washing the slide, and repeating the hybridization using four different libraries similarly labeled. It should be apparent that the number of libraries that can be distinguished using the instant scheme is comparable to the number of probe sets that can be measured using current methods.

The maximum number of targets that can be identified using the instant method is defined by the number libraries used, where the maximum number of targets that can be identified is $2^n-1$, where n is the number of libraries. For example, if 4 libraries are used then 15 different targets can be identified, if 8 libraries are used then 255 targets can be identified, and if 12 libraries are used, then 4095 different targets can be identified, and so on. This exponential increase in the number of targets that can be identified provides a significant advantage over prior art methods.

Because, in practice, there is often a limited number of distinguishable labels that can be readily obtained, performance of the instant method using higher numbers of libraries (e.g., more than 3 or 4 libraries) in certain cases may be more readily accomplished using successive hybridizations, where each hybridization is done using a plurality of libraries that are distinguishably labeled from one another. For example, in one embodiment, 255 probe sets can be combined into eight libraries, and the eight libraries hybridized as two successive hybridizations on the same sample (where probes hybridized in the first hybridization are stripped prior to the second hybridization). In this embodiment, the libraries used in the first hybridization are distinguishably labeled from one another (e.g., using four distinguishable dyes), and the libraries used in the second hybridization are distinguishably labeled from one another (e.g., using the same four distinguishable dyes as used in the first hybridization). Further advantages over the prior art may be realized in performing such a method.

Certain hybridization methods used herein include the steps of fixing a biological or non-biological sample (e.g., containing cells), hybridizing labeled libraries to RNA or DNA molecules contained within the fixed sample, and washing the hybridized sample to remove non-specific binding. In situ hybridization assays and methods for sample preparation are well known to those of skill in the art and need not be described in detail here. Such methods can be found in, for example, Amann R. et al., 1995, Microbiol. Rev. 59(1): 143-69; Bruns and Berthe-Corti, 1998, Microbiology 144, 2783-2790; Vesey G. et al., 1998, J. App. Microbiol. 85, 429-440; and Wallner G. et al., 1995, Appl. Environ. Microbiol. 61(5): 1859-1866, and US20100081131, which are incorporated by reference herein.

Certain fluorescence in situ hybridization (FISH) methods offer many advantages over radioactive and chromogenic methods for detecting hybridization. Not only are fluorescence techniques fast and precise, they allow for simultaneous analysis of multiple signals that may be spatially overlapping. Through use of appropriate optical filters, it is possible to distinguish multiple different fluorescent signals in a single sample using their excitation and emission properties alone. Methods for combinatorial labeling are described in, e.g., see, Ried et al., 1992, Proc. Natl. Acad. Sci. USA 89, 1388-1392; Tanke, H. J. et al, 1999, *Eur. J. Hum. Genet.* 7: 2-11. By using combined binary ratio labeling (COBRA) in conjunction with highly discriminating optical filters and appropriate software, over 40 signals can be distinguished in the same sample, see, e.g., Wiegant J. et al., 2000, Genome Research, 10 (6), 861-865.

In certain embodiments, microbial cells are harvested from a biological or non-biological sample using standard techniques. For example, cells can be harvested by centrifuging a sample and resuspending the pelleted cells in, for example, phosphate-buffered saline (PBS). After re-centrifuging the cell suspension to obtain a cell pellet, the cells can be fixed in a solution such as an acid alcohol solution, an acid acetone solution, or an aldehyde such as formaldehyde, paraformaldehyde, or glutaraldehyde. For example, a fixative containing methanol and glacial acetic acid in a 3:1 ratio, respectively, can be used as a fixative. A neutral buffered formalin solution also can be used (e.g., a solution containing approximately 1% to 10% of 37-40% formaldehyde in an aqueous solution of sodium phosphate). Slides containing the cells can be prepared by removing a majority of the fixative, leaving the concentrated cells suspended in only a portion of the solution. Methods for fixing microbes are known in the art and can be adapted to suit different types of microbes, if needed. Determination of suitable fixation/permeabilization protocols are carried out routinely in the art.

In some embodiments, a secondary detection method may be employed to amplify the signal, for example. However, polynucleotide probes can be sufficiently sensitive to detect a single molecule in situ. In addition, molecular beacons that are labeled with a fluorophore and a quencher can provide the sensitivity required to detect about 10 molecules in a single cell in situ without the need for amplification. Prior to in situ hybridization, the oligonucleotides may be denatured. Denaturation is typically performed by incubating in the presence of high pH, heat (e.g., temperatures from about 70° C. to about 95° C.), organic solvents such as formamide and tetraalkylammonium halides, or combinations thereof.

Permeabilized/fixed cells are contacted with labeled polynucleotides under in situ hybridizing conditions, where "in situ hybridizing conditions" are conditions that facilitate annealing between a nucleic acid and the complementary nucleic acid. Hybridization conditions vary, depending on the concentrations, base compositions, complexities, and lengths of the probes, as well as salt concentrations, temperatures, and length of incubation. For example, in situ hybridizations typically are performed in hybridization buffer containing 1-2×SSC, 50% formamide, and blocking DNA to suppress non-specific hybridization. In general, hybridization conditions include temperatures of about 25° C. to about 55° C., and incubation times of about 0.5 hours to about 96 hours. Suitable hybridization conditions for a library of oligonucleotides and target microbe can be determined via experimentation which is routine for one of skill in the art.

The microbes might be present in a suspension or alternatively, the microbes may be immobilized on a substrate. Immobilization of the microbes might be desirable in applications where additional microscopic features, such as, morphology of the microbe is to be assessed. Obviously, a suspension of microbes might be sorted into different types of microbes based on the predetermined optically detectable signature, followed by immobilization of the microbes.

A hybridized sample can be read using a variety of different techniques, e.g., by microscopy, such as light microscopy, fluorescent microscopy or confocal microscopy. In embodiments in which oligonucleotides are labeled with a fluorescent moiety, reading of the contacted sample to detect hybridization of labeled oligonucleotides may be carried out by fluorescence microscopy. Fluorescent microscopy or confocal microscopy used in conjunction with fluorescent microscopy has an added advantage of distinguishing multiple labels even when the labels overlap spatially. Methods of reading fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park: Benjamin/Cummings Publishing Col, Inc. (1978), pp. 296-361.

The method may further comprise determining which of the multiple libraries hybridized to a spatially-separated target. Once the sample is read, the identities of targets in the sample can be determined by determining which of the libraries a target hybridized to. For example, with reference to Table 1 above, the target of probe set P15 (which may be, e.g., a species or a strain of microbe) can be identified as being P15 because it hybridized with probes that are present in all four libraries. Likewise, the target of probe set P7 can be identified as being P7 because it hybridized with probes that are present in L2, L3 and L4, but not L1. As such, in some embodiments, the method may further comprise determining the identity of a spatially separated target by which combination of the multiple libraries hybridize to it. This may be done using a look-up table, similar to those shown above and below.

FIG. 1 illustrates prophetic results of an assay in which four libraries (such as the four libraries shown in Table 1 above) are hybridized against a population that contains 15 types of microbe. By determining which libraries hybridize with which targets, the identity of the target can be determined. For example, the cell marked in the top left can be identified as a "P12" cell because it hybridizes with L1 and L2, whereas, for example, the cell to the right of P12 can be identified as a P8 cell because it only hybridizes with L1. This method can also be used to simultaneously detect, e.g., hundreds to thousands of RNA transcripts in fixed cells. In fact, any in situ hybridization measurement known to the art can be exponentially multiplexed using the methods described herein. In certain embodiments, the most abundant RNA targets may be encoded using codes with the fewest bits (i.e. probe sets targeting the most abundant targets occur only in one library, the next most abundant only in two, etc.) so as to minimize the average total label density observed for each library. For applications labeling entire cells there should be little ambiguity associating cells among libraries.

In certain cases (particularly those in which the libraries are being prepared for use in an RNA in situ hybridization assay), it may be advantageous to select the probe sets in such a way that, when all of the libraries have been hybridized to a cell, the total number of hybridized targets is minimized and the number of hybridized targets is spread out as evenly as possible among the libraries. In certain cases, the probe sets may be distributed in the libraries so that each library is predicted to provide an approximately equal number of hybridized targets. So, in these embodiments, a probe set to a target predicted to occur in very high abundance may be included in only one library (which reduces the total number of hybridized targets from the other libraries). Conversely, probe sets to low abundance targets may be placed in many libraries, since they should not produce many hybridized targets. One scheme for dealing these out is to sort the probe sets high to low by predicted target abundance, and select them for inclusion into the various libraries in order, e.g. P1→L1, P2→L2, Pn→Ln, Pn+1→Ln+Ln−1, Pn+2→Ln−1+Ln−2, ... P2n−1→L1+L2, P2n→L1+L2+L3, etc., (where n is the number of libraries). Use of this method may ensure that hybridized targets (i.e., the RNA molecules) within a single a cell are more likely to be spatially separated by more than the optical resolution of the microscope, which provides more robust results.

As illustrated in Table 2 below, the method may also include an error correction system so that if any one hybridization fails, useful data can still be obtained. In one embodiment, the combining may include an error correcting (7,4) Hamming code, for example. In the example shown below, libraries L3, L5, L6, L7 encode the data, and L1p, L2p, L4p encode parity bits. Any single FP or FN error can be corrected using this scheme, and the occurrence of two errors can be detected. Any of the schemas shown above or below may be generalized to larger numbers of libraries. Such schemes allow for simultaneous identification of N targets by measuring only on the order of log 2(N) library hybridizations.

TABLE 2

|     | L1p | L2p | L3 | L4p | L5 | L6 | L7 |
|-----|-----|-----|----|-----|----|----|----|
| P1  | 1   | 1   | 0  | 1   | 0  | 0  | 1  |
| P2  | 0   | 1   | 0  | 1   | 0  | 1  | 0  |
| P3  | 1   | 0   | 0  | 0   | 0  | 1  | 1  |
| P4  | 1   | 0   | 0  | 1   | 1  | 0  | 0  |
| P5  | 0   | 1   | 0  | 0   | 1  | 0  | 1  |
| P6  | 1   | 1   | 0  | 0   | 1  | 1  | 0  |
| P7  | 0   | 0   | 0  | 1   | 1  | 1  | 1  |
| P8  | 1   | 1   | 1  | 0   | 0  | 0  | 0  |
| P9  | 0   | 0   | 1  | 1   | 0  | 0  | 1  |
| P10 | 1   | 0   | 1  | 1   | 0  | 1  | 0  |
| P11 | 0   | 1   | 1  | 0   | 0  | 1  | 1  |
| P12 | 0   | 1   | 1  | 1   | 1  | 0  | 0  |
| P13 | 1   | 0   | 1  | 0   | 1  | 0  | 1  |

TABLE 2-continued

|  | L1p | L2p | L3 | L4p | L5 | L6 | L7 |
|---|---|---|---|---|---|---|---|
| P14 | 0 | 0 | 1 | 0 | 1 | 1 | 0 |
| P15 | 1 | 1 | 1 | 1 | 1 | 1 | 1 |

In one embodiment, the target-specific probe sets are physical entities (e.g., BACs, oligonucleotides or PCR products) that are contained in a vessel. In another embodiment, the target-specific probe sets are represented by nucleotide sequences (e.g., oligonucleotide sequences) that are present in electronic form, i.e., in silico. In physical embodiments, the separate probe sets may be physically combined to make the multiple libraries, as described above. In in silico embodiments, the sequences of the probe sets may be combined using a computer to produce multiple lists of sequences (where, e.g., each list corresponds to all of the probes in all of the probe sets of a library). After the lists are produced, the different libraries can be made and used in accordance with the methods set forth above.

In embodiments that employ oligonucleotides, the different libraries may be made in the form of an array. In certain embodiments, the array may be synthesized using in situ synthesis methods in which nucleotide monomers are sequentially added to a growing nucleotide chain that is attached to a solid support in the form of an array. Such in situ fabrication methods include those described in U.S. Pat. Nos. 5,449,754 and 6,180,351 as well as published PCT application no. WO 98/41531, the references cited therein, and in a variety of other publications. In one embodiment, the oligonucleotides may be made by fabricating an array of the oligonucleotides using in situ synthesis methods, and cleaving oligonucleotides from the array.

In certain embodiments in which oligonucleotides are used, the various libraries may contain oligonucleotides of the formula $X_1$—$V$—$X_2$ (from 5' to 3'), where $X_1$ and $X_2$ provide binding sites for a pair of PCR primers (e.g., where $X_1$ has the same sequence as a first PCR primer and $X_2$ has a sequence that is complementary to a second PCR primer), and V is a variable region that has a nucleotide sequence selected by the above described method, as described in US20100055681, which is incorporated by reference. The variable region may be amplified by the pair of PCR primers. The primer binding sites may be 15-40 (e.g., 18 to 30) nucleotides in length, and the variable region (having the FISH probe oligonucleotide sequence selected by the subject method) may be in the range of 90 to 180 (e.g., 100-150) nucleotides in length, although primer binding sites and variable regions outside of these ranges are envisioned. In these embodiments, the oligonucleotides in each library may have similar binding characteristics in that they may be Tm-matched and have a similar GC content, etc.

In particular embodiments, the different libraries may be made on different arrays. In one embodiment, all libraries may be made on a single array, and each of the libraries has different $X_1$ and $X_2$ sequences such that each library can be PCR amplified independently from the other libraries. In this embodiment, an array containing multiple oligonucleotide libraries is made, the oligonucleotides are cleaved from the array, and the individual libraries are PCR amplified, labeled, and used in the method described above.

In addition to the method described above, a set of reagents is provided. In certain embodiments, the set of reagents comprises: a) a plurality of target-specific probe sets that each comprise a different population of target-specific polynucleotide probes; and b) multiple libraries made from the plurality of target-specific probe sets, wherein each of the libraries is composed of a different combination of the target-specific probe sets. The multiple libraries may be labeled, e.g., with the same label or with different labels that are distinguishable relative to one another.

The method is illustrated using polynucleotide probes (e.g., oligonucleotide probes) as an example. As would be readily apparent, the method may be readily adapted for use with other types of probes, e.g., antibodies, aptamers, etc., without undue effort. It should be evident that measurements other than FISH which rely on measuring single molecules targeted by labeled probes would also benefit from the methods described. For example, immunohistochemical measurements of proteins, glycans, metabolites, cell surface markers, or other target molecules, which are typically (but not necessarily) probed using labeled antibodies, could be multiplexed using these methods.

Also provided by the subject invention are kits for practicing the subject method, as described above. The subject kit, which may be in the form of a larger containing smaller containers, may contain any combination of the reagents described above. Certain kits may also contain a reference sample to be employed as a control in the subject method.

The various components of the kit may be present may be each present in separate vessels, or combined in one or more vessels. The various components of the kit may be in solution, e.g., in aqueous solution which in certain cases may be frozen, or in dried form for example. In one embodiment, a kit may comprise a set of reagents as described above (which may be in dried form, for example), and information (e.g., a look-up table which may be in paper form) that describes which targets (e.g., which species of microbe) the various libraries hybridize to. Combined, the reagents and information allow a user to perform the method described above, and deconvolute the results to identify which targets are present in their sample. In some cases, the kit may further contain reagents for labeling the probes, and/or reagents for in situ hybridization (e.g., fixation and hybridization reagents).

In addition to above-mentioned components, the subject kit may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the instructions, the kits may also include one or more control analyte mixtures, e.g., two or more control analytes for use in testing the kit.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A set of reagents comprising:
 a plurality of at least three probe libraries, wherein the probe libraries are in solution and:
  (i) each library of said plurality comprises one or more probe sets that are each specific for a target;
  (ii) at least one of said libraries comprises a probe set that is present in another of said libraries; and
  (iii) each probe set is specific for a different microbe relative to other probe sets in said libraries.

2. The set of reagents of claim 1, wherein each probe set is uniquely defined by the set of libraries that contain said probe set.

3. The set of reagents of claim 1, wherein said set of reagents comprises at least four of said probe libraries.

4. The set of reagents of claim 1, wherein said probe libraries comprise oligonucleotides.

5. The set of reagents of claim 1, wherein said at least three probe libraries are labeled.

6. The set of reagents of claim 5, wherein said at least three probe libraries are all labeled with the same label.

7. The set of reagents of claim 5, wherein said at least three probe libraries are distinguishably labeled relative to one another.

8. The set of reagents of claim 1, wherein said target-specific probe sets are cell type specific.

9. The set of reagents of claim 8, wherein said target-specific probe sets are species specific.

10. The set of reagents of claim 1, wherein the target-specific probe sets hybridize to RNA molecules, and the probe sets are distributed among said libraries so as to minimize the expected total number of hybridized targets.

11. A kit comprising:
 a) a set of reagents comprising: a plurality of at least three probe libraries, wherein the probe libraries are in solution and:
  (i) each library of said plurality comprises one or more probe sets that are each specific for a target;
  (ii) at least one of said libraries comprises a probe set that is present in another of said libraries; and
  (iii) each probe set is specific for a different microbe relative to other probe sets in said libraries; and
 b) information that describes which targets said at least three libraries hybridize to.

* * * * *

UNITED STATES PATENT AND TRADEMARK OFFICE
CERTIFICATE OF CORRECTION

| | | |
|---|---|---|
| PATENT NO. | : 8,765,642 B2 | Page 1 of 1 |
| APPLICATION NO. | : 13/448985 | |
| DATED | : July 1, 2014 | |
| INVENTOR(S) | : Bo U. Curry | |

It is certified that error appears in the above-identified patent and that said Letters Patent is hereby corrected as shown below:

On the Title Page, Item (73), in column 1, in "Assignee", line 1, delete "Technolgies" and insert -- Technologies --, therefor.

Signed and Sealed this
Thirty-first Day of March, 2015

Michelle K. Lee
*Director of the United States Patent and Trademark Office*